(12) United States Patent
Lewisch et al.

(10) Patent No.: US 10,088,490 B2
(45) Date of Patent: Oct. 2, 2018

(54) ASSAY FOR ANALYTES USING MULTIPLE RECEPTORS

(75) Inventors: Sandra A. Lewisch, Bear, DE (US); Lynn M. Schiavoni, Newark, DE (US); William D. Bedzyk, Odessa, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 877 days.

(21) Appl. No.: 12/860,600

(22) Filed: Aug. 20, 2010

(65) Prior Publication Data

US 2012/0045847 A1 Feb. 23, 2012

(51) Int. Cl.
| | | |
|---|---|---|
| G01N 33/74 | (2006.01) | |
| G01N 33/536 | (2006.01) | |
| G01N 33/53 | (2006.01) | |
| G01N 33/94 | (2006.01) | |

(52) U.S. Cl.
CPC ......... *G01N 33/743* (2013.01); *G01N 33/536* (2013.01); *G01N 33/5306* (2013.01); *G01N 33/9493* (2013.01)

(58) Field of Classification Search
None
See application file for complete search history.

(56) References Cited

U.S. PATENT DOCUMENTS

| | | |
|---|---|---|
| 3,985,867 A | 10/1976 | Redshaw |
| 4,376,110 A | 3/1983 | David et al. |
| 4,514,505 A | 4/1985 | Canfield et al. |
| 4,722,889 A | 2/1988 | Lee et al. |
| 4,737,456 A | 4/1988 | Weng et al. |
| 4,792,528 A | 12/1988 | Canfield et al. |
| 5,447,846 A | 9/1995 | Shinoki et al. |
| 5,518,887 A | 5/1996 | Parsons et al. |
| 5,612,016 A | 3/1997 | Griffiths et al. |
| 7,141,378 B2 * | 11/2006 | Miller et al. ................ 435/6.12 |
| 7,229,763 B2 * | 6/2007 | Reddy et al. ............... 435/6.16 |
| 2008/0003617 A1 | 1/2008 | Fan et al. |
| 2009/0005267 A1 | 1/2009 | Love et al. |

OTHER PUBLICATIONS

Lewisch et al., "Development of a Cortisol Assay using LOCI® technology on the Dimension® Vista Intelligent Lab System", Clinical Chemistry vol. 55, No. 6, Supplement, Jun. 2009, abstract D-113, pp. A186-A187, retrieved from http://www.aacc.org/events/annualmtgdirectory/Documents/Wednesday-PM-7-22-AACC-Abstracts-09.pdf.*
Chul et al, "Interference of 6[beta]-Hydroxycortisol in the Quantitation of Urinary Free Cortisol by Immunoassay and Its Elimination by Solid Phase Extraction", Clinical Biochemistry, Jan. 1, 1998, pp. 229-233.
International Search Report and Written Opinion of International Application No. PCT/US2011/048107 dated Dec. 21, 2011.
European Search Report and Written Opinion of European Application No. EP 11818734 dated Jan. 14, 2014.

* cited by examiner

*Primary Examiner* — Christine Foster
(74) *Attorney, Agent, or Firm* — Cynthia G. Tymeson

(57) ABSTRACT

A method for determining an analyte in a sample suspected of containing the analyte comprises providing in combination a medium, the sample, and two or more different receptors. Each different receptor binds to at least two different epitopic sites. One of the epitopic sites is a common binding site and one of the epitopic sites is non-common binding site. The non-common epitopic sites are different for each different receptor. The receptors exhibit mono-molecular binding. The medium is incubated under conditions for binding of the receptors to the epitopic sites. The medium is examined for the presence and/or amount of complexes comprising the epitopic sites and the receptors. The presence and/or amount of the complexes indicate the presence and/or amount of the analyte in the sample.

5 Claims, 2 Drawing Sheets

ASSAY FOR ANALYTES USING MULTIPLE RECEPTORS

BACKGROUND

The present invention relates generally to compositions and methods useful for determining the presence of analytes.

The clinical diagnostic field has seen a broad expansion over the years, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized as well as the presence of substances that interfere with the detection of the analyte by cross-reacting with reagents used in the detection of an analyte. Signal-dose response to changes in the concentration of analyte and the presence of cross-reactants in a sample are important considerations in assay development.

There is a continuing need to modulate cross-reactivity and signal-dose response in assays for determining an analyte in a sample.

SUMMARY

One embodiment of the present invention is a method for determining an analyte in a sample suspected of containing the analyte. A combination is provided comprising a medium, the sample, and two or more different receptors. Each different receptor binds to at least two different epitopic sites. One of the epitopic sites is a common binding site and one of the epitopic sites is non-common binding site. The non-common epitopic sites are different for each different receptor. The receptors exhibit mono-molecular binding. The medium is incubated under conditions for binding of the receptors to the epitopic sites. The medium is examined for the presence and/or amount of complexes comprising the epitopic sites and the receptors. The presence and/or amount of the complexes indicate the presence and/or amount of the analyte in the sample.

In some embodiments of the above method, each different receptor is part of a different receptor-tracer conjugate. The tracer of each different receptor-tracer conjugate is the same and the receptor of each different receptor-tracer conjugate is different. In the above method the medium is examined for the presence and/or amount of complexes comprising the epitopic sites and the receptor-tracer conjugates. The presence and/or amount of the complexes indicate the presence and/or amount of the analyte in the sample.

In some embodiments of the above method, the combination further comprises an analyte analog-tracer conjugate. The medium is examined for the presence and/or amount of complexes comprising the receptors and the analyte analog-tracer conjugates where the presence and/or amount of the complexes indicate the presence and/or amount of the analyte in the sample.

Another embodiment of the present invention is a method for determining a small molecule analyte in a sample suspected of containing the small molecule analyte and one or more different interfering substances. A combination is provided comprising a medium, the sample, and two or more different antibody-tracer conjugates. The tracer of each different conjugate is the same and the antibody of each different conjugate is different. Each different antibody binds to at least two different epitopic sites wherein one of the epitopic sites is a common binding site and one of the epitopic sites is non-common binding site. The non-common epitopic sites are different for each different antibody and each of the non-common epitopic sites are present on a respective interfering substance. The antibody-tracer conjugates exhibit mono-molecular binding. The medium is incubated under conditions for binding of the different antibodies to the epitopic sites and examined for the presence and/or amount of complexes comprising the epitopic sites and the antibody-tracer conjugates. The presence and/or amount of the complexes indicate the presence and/or amount of the analyte in the sample.

Another embodiment of the present invention is a method of modulating one of both of cross-reactivity and signal-dose response in an assay for determining an analyte in a sample suspected of containing the analyte. A combination is provided in a medium. The combination comprises the sample and two or more different receptors. Each different receptor is selected for its binding profile to the analyte and to one or more interfering substances. The amount of each different receptor-tracer conjugate in the medium is chosen such that cross-reactivity and signal-dose response in the assay is modulated. The medium is incubated under conditions for binding of the receptors to the analyte and to the interfering substances. The medium is examined for the presence and/or amount of complexes comprising the receptors where the presence and/or amount of the complexes indicate the presence and/or amount of the analyte in the sample.

DETAILED DESCRIPTION OF SPECIFIC EMBODIMENTS

Figure 1:
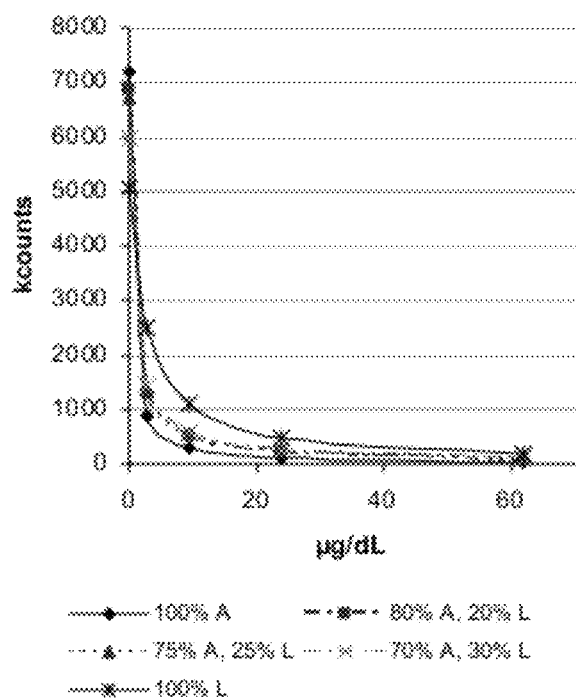
FIG. 1 is a calibration curve from a method in accordance with an example of an embodiment of the present disclosure showing instrument signal plotted as a function of the concentration of cortisol.

In some embodiments the present invention is a method of modulating one or both of cross-reactivity and signal-dose response in an assay for determining an analyte in a sample suspected of containing the analyte. As used herein "cross-reactivity" means the reaction of one or more interfering substances present in a sample suspected of containing the analyte with one or more of the reagents employed in the detection of the analyte. An interfering substance (or cross-reactant) is any molecule or part of a molecule that interferes in the detection of an analyte by reacting with one or more of the reagents employed in the detection of the analyte. The interfering substance may be mono-epitopic or poly-epitopic. An "epitopic site" or "epitope" is an area on the surface or in a cavity of a molecule where the area is specifically recognized and binds to a particular spatial and polar organization of another molecule. A "mono-epitopic" molecule is a molecule that has only one epitopic site. A "poly-epitopic" molecule is a molecule that has two or more different epitopic sites, or three or more different epitopic sites, or four or more different epitopic sites, or five or more epitopic sites, for example.

In some embodiments the interfering substances are structurally similar to the analyte. The interfering substances may be metabolites of the analyte, analogs of the analyte, synthetic precursors of the analyte, for example.

The single epitope of a mono-epitopic interfering substance may react with one or more reagents used in the detection of the analyte. On the other hand, one epitope (non-detection epitope) of a poly-epitopic analyte may react with one or more reagents that are employed in the detection of the analyte where the one or more reagents are specific for another epitope (detection epitope) of a poly-epitopic analyte. The presence of the detection epitope is indicative of the presence of the analyte in a sample. In other words the detection epitope is that epitopic site that is specific for the detection of the analyte in an assay. The interfering substance also may be a fragment of a larger molecule where the fragment comprises one epitope of a poly-epitopic molecule.

By "signal-dose response" or "standard curve" or "dose response" is meant a curved or substantially linear line drawn to connect at least two sample dosage data points corresponding to individual sample dose analyses. Curved lines are present for assays having nonlinear dose response curves over the range of sample analyte values while straight lines are present for assays having linear dose response curves over the range of sample analyte values. Instrument signals may increase or decrease with increasing analyte concentration, depending on the assay format that is employed in a particular determination.

In some embodiments of the present methods, a sample suspected of containing an analyte is combined in a suitable assay medium with two or more different receptors. The number of different receptors employed is dependent on one or more of the nature of the analyte, the nature of the interfering substances, or the nature of the receptor including the binding properties of the receptor to the analyte, the binding properties of the receptor to interfering substances, and the nature of the signal-dose response curve, for example. The number of different receptors may be two, or three, or four, or five or more and may be in the range of 2 to about 10, or 2 to about 8, or 2 to about 6, or 2 to about 4, or 2 to 3, or 3 to about 10, or 3 to about 8, or 3 to about 6, or 3 to 4, or 4 to about 10, or 4 to about 8, or 4 to about 6, or 4 to 5, for example.

The term "conjugate" in the context of "receptor-tracer conjugate" or "antibody-tracer conjugate" means a receptor or an antibody, respectively, which is bound either covalently or non-covalently to a tracer. The tracer of each different conjugate is the same and the receptor or antibody of each different conjugate is different. The tracer may be any molecule that is involved either directly or indirectly in the generation of a signal in the assay that corresponds to the presence of the analyte in a sample. The tracer is part of a signal producing system ("sps"), which may have one or more components, at least one component being the tracer. The signal producing system generates a signal that relates to the presence of an analyte in a sample. The signal producing system includes all of the reagents required to produce a measurable signal. Other components of the signal producing system can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like.

The tracer is capable of being detected directly or is detectable indirectly through, for example, a specific binding reaction that binds the tracer to a moiety that comprises a signal-generating component that produces a detectable signal. The tracer may be isotopic or non-isotopic, and can be, by way of illustration and not limitation, a polynucleotide coding for a catalyst, a promoter, a dye, a fluorescent molecule, a chemiluminescent molecule, a sensitizer including photosensitizers, an enzyme, a coenzyme, an enzyme substrate, a radioactive group, a small organic molecule, an amplifiable polynucleotide sequence, a support such as, for example, a particle such as, e.g., a latex or carbon particle, a metal sol, a crystallite, a liposome, a cell, a microtiter plate, for example. In some embodiments the support may or may not be further labeled with a dye, catalyst or other detectable group, for example. Tracers that are small organic molecules are members of a specific binding pair ("sbp member(s)") such as, for example, biotin-avidin, digoxin-antidigoxin, digoxigenin-antidigoxigenin, and dinitrophenol-antidinitrophenol.

A receptor is a molecule having an area on the surface or in a cavity, which specifically binds to and is thereby defined as complementary with a particular spatial and polar organization of another molecule. The receptor may be an antibody, avidin or streptavidin, a hormone receptor, an enzyme, a nucleic acid including DNA and RNA, and protein A, for example.

Each different receptor is selected for its binding profile or cross-reactivity profile to the analyte and to one or more interfering substances. The phrase "binding profile" or "cross-reactivity profile" refers to the binding properties of a receptor with respect to an analyte and to a predetermined or select group of interfering substances. The number of interfering substances included in the predetermined group for determining a binding profile is based on one or more of the nature of the analyte, the nature of metabolites of the analyte, the nature of the sample, the nature of the receptor, the binding properties of the receptor to the analyte and interfering substances and the nature of the structurally similar compounds known or suspected to be present in a sample, for example. Each receptor selected should exhibit a sufficient level of binding to the analyte, which means that each receptor must have a binding affinity for the analyte suitable to be used in the selected assay system to achieve an accurate determination of the presence and/or amount of such analyte. Receptors with a sufficient binding affinity for the analyte may be selected by well known screening methodologies and include, by way of illustration and not limitation, ELISA, dot blots, Western analysis, and Surface Plasmon Resonance, for example.

Each different receptor should also exhibit low binding affinity to at least a portion of the interfering substances. The phrase "low binding affinity" means that the receptor should have a binding affinity for an interfering substance no greater than about 80% of that for the analyte, or no greater than 70% of that for that analyte, or no greater than about 60% of that for the analyte, for example. The binding affinity of the receptor for the interfering substances may be determined by well known techniques and include, by way of illustration and not limitation, ELISA and Surface Plasmon Resonance, for example. In an alternative approach the percent cross-reactivity between the receptor and the interfering substances is determined. The percent cross-reactivity between the receptor and the interfering substances may be determined by conducting a selected assay according to the assay protocol in the presence and absence of the potentially interfering substance and comparing the signal response in each example (with or without the potentially interfering substance) at analyte concentrations of clinical significance, i.e., at the medical decision level.

The number of interfering substances in the portion to which the receptor exhibits low binding affinity is dependent on one or more of the total number of the interfering substances suspected of being present in a sample, the nature of the analyte, the nature of the interfering substances, the nature of the sample, the nature of the receptor, and the binding properties of the receptor to the analyte and to the interfering substances, for example. The portion of the interfering substances may comprise as few as one member and no more than the total number of interfering substances minus one. The portion of the interfering substances may range from about 10% to about 90%, or about 10% to about 80%, or about 10% to about 70%, or about 10% to about 60%, or about 10% to about 50%, or about 10% to about 40%, or about 10% to about 30%, or about 10% to about 20% of the total number of interfering substances.

In addition, there should be minimal overlap between a portion of the interfering substances that have low binding affinity for one receptor and a portion of the interfering substances that have low binding affinity for another receptor. The phrase "minimal overlap" means that the number of interfering substances in one portion that have low binding affinity for two different receptors should not be greater than about 10, or about 9, or about 8, or about 7, or about 6, or about 5, or about 4, or about 3, or about 2, or 1, for example. The number of different receptors employed should be sufficient such that the low binding affinity of the mixture of receptors applies to substantially all of the interfering substances. By the phrase "substantially all of the interfering substances" is meant that the number of interfering substances not covered by the mixture of receptors is less than about 10%, or less than about 5%, or less than about 4%, or less than about 3%, or less than about 2%, or less than about 1% of the total number of interfering substances.

As mentioned above, each receptor is different and each different receptor binds to at least two different epitopic sites. The difference in the receptors results from one of the epitopic sites to which the receptor binds being a common binding site and one of the epitopic sites to which the receptor binds being a non-common binding site. A common binding site is an epitopic site that is the same for all of the receptors employed and each receptor is capable of binding to the common binding site. The phrase "the same" means that the receptor has specificity for the common binding site but does not bind to the same molecule that comprises the common binding site, but rather binds to a molecule that has a free common binding site. In that regard the receptors exhibit mono-molecular binding, which means that one molecule of receptor binds to only one molecule that comprises the common binding site. The common binding site may be a single epitope of a mono-epitopic analyte or it may be one epitope of a poly-epitopic analyte.

The non-common epitopic sites to which each different receptor binds are different for each different receptor. For mono-epitopic analytes the non-common epitopic sites are present on interfering substances. For poly-epitopic analytes the non-common epitopic sites may be one or both of epitopic sites other than the common binding site on a poly-epitopic analyte or epitopic sites present on interfering substances. As mentioned above, the receptors exhibit mono-molecular binding.

The receptor can be linked to the tracer covalently either directly by a bond or through the intermediacy of a linking group. In some embodiments the preparation of receptor-tracer conjugates may be carried out by employing functional groups suitable for attaching the tracer to the receptor by a direct bond. The nature of the functional groups employed is dependent on one or more of the nature of the tracer, the nature of the receptor, the nature of the analyte and the nature of the reaction mixture, for example. For example, a large number of suitable functional groups are available for attaching to amino groups and alcohols; such functional groups include, for example, activated esters including, e.g., carboxylic esters, imidic esters, sulfonic esters and phosphate esters; activated nitrites; aldehydes; ketones; and alkylating agents.

The linking group may be a chain of from 1 to about 60 or more atoms, or from 1 to about 50 atoms, or from 1 to about 40 atoms, or from 1 to 30 atoms, or from about 1 to about 20 atoms, or from 1 to about 10 atoms, each independently selected from the group normally consisting of carbon, oxygen, sulfur, nitrogen, and phosphorous, usually carbon and oxygen. The number of heteroatoms in the linking group may range from about 0 to about 8, from about 1 to about 6, or about 2 to about 4. The atoms of the linking group may be substituted with atoms other than hydrogen such as, for example, one or more of carbon, oxygen and nitrogen in the form of, e.g., alkyl, aryl, aralkyl, hydroxyl, alkoxy, aryloxy, or aralkoxy groups. As a general rule, the length of a particular linking group can be selected arbitrarily to provide for convenience of synthesis with the proviso that there is minimal interference caused by the linking group with the ability of the linked molecules to perform their function related to the assay in question.

The linking group may be aliphatic or aromatic. When heteroatoms are present, oxygen will normally be present as oxy or oxo, bonded to carbon, sulfur, nitrogen or phosphorous; sulfur will be present as thioether or thiono; nitrogen will normally be present as nitro, nitroso or amino, normally bonded to carbon, oxygen, sulfur or phosphorous; phosphorous will be bonded to carbon, sulfur, oxygen or nitrogen, usually as phosphonate and phosphate mono- or diester. Functionalities present in the linking group may include esters, thioesters, amides, thioamides, ethers, ureas, thioureas, guanidines, azo groups, thioethers, carboxylate and so forth. The linking group may also be a macro-molecule such as polysaccharides, peptides, proteins, nucleotides, and dendrimers.

In some embodiments the receptor and the tracer may be linked together non-covalently. Members of a binding pair, usually a specific binding pair, are employed where one member is linked to the receptor and the other member is linked to the tracer. Binding of the binding pair members results in the non-covalent linking of the receptor and the tracer. The binding pair members may be linked directly to one or both of the receptor and the tracer or indirectly through the intermediacy of a linking group, the nature of which is discussed above. A member of a specific binding pair is one of two different molecules having an area on the surface or in a cavity, which specifically binds to and is thereby defined as complementary with a particular spatial and polar organization of the other molecule. The members of the specific binding pair may be members of an immunological pair such as antigen-antibody or hapten-antibody, biotin-avidin, hormones-hormone receptors, enzyme-substrate, nucleic acid duplexes, IgG-protein A, and polynucleotide pairs such as DNA-DNA, DNA-RNA, for example.

The receptor-tracer conjugates can be prepared by linking each different receptor in separate, individual reactions to the tracer and then combining the receptor-tracer conjugates to form a mixture comprising the receptor-tracer conjugates. Alternatively, the different receptors can be combined and the reaction to link the receptors to the tracer can be carried out on the combination.

The percentage amount of each different receptor in the medium is chosen such that cross-reactivity and signal-dose response in the assay is modulated. The percentage amounts of each different receptor are not critical; however, in some embodiments one percentage may be preferred over another. The percentage amounts of the receptors are determined for each individual assay system. For example, by way of illustration and not limitation, in a two receptor system, the range can be between 1% to about 99% for the first receptor with the balance made up by the second receptor. For systems using three or more receptors, again by way of illustration and not limitation, each receptor may represent at least 1%, or at least about 2%, or at least about 5%, or at least about 10%, or at least about 15%, or at least about 20% of the total number of receptors used.

The following discussion is directed to antibodies by way of illustration and not limitation; the present embodiments have application to all types of assays in which one or more receptors are employed for the determination of an analyte.

Antibodies that are utilized may be polyclonal or monoclonal. The nature of the antibody depends on one or more of the specificity of the antibody, the binding affinity (Kd) of the antibody, the kinetics of the binding between the antibody and a complementary molecule, for example. The antibody may include a complete immunoglobulin or fragment thereof, which immunoglobulins include the various classes and isotypes, such as IgA, IgD, IgE, IgG1, IgG2a, IgG2b and IgG3, IgM, etc. Fragments (including recombinant fragments) thereof may include Fab, Fv and F(ab')$_2$, Fab', and the like. In addition, aggregates, polymers, and conjugates of immunoglobulins or their fragments can be used.

The polyclonal antibodies and the monoclonal antibodies may be prepared by techniques that are well known in the art. For example, in one approach monoclonal antibodies are obtained by somatic cell hybridization techniques. Monoclonal antibodies may be produced according to the standard techniques of Köhler and Milstein, *Nature* 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981). In general, monoclonal antibodies can be purified by known techniques such as chromatography, e.g., DEAE chromatography, ABx chromatography, and HPLC chromatography, for example; filtration, and so forth.

An example of a screening method for selecting antibodies having a desired binding profile is described below by way of illustration and not limitation using monoclonal antibodies as an example. A sample suspected of containing an analyte may also contain ten interfering substances (IS 1-10) that might impact the sensitivity and specificity of an assay for the detection of the analyte by cross-reaction with the monoclonal antibody. Monoclonal antibodies are obtained or prepared that have specificity for the analyte. The monoclonal antibodies are screened by employing an assay method utilizing each different monoclonal antibody-tracer conjugate in an assay for each of IS 1-10. An appropriate assay medium is employed for the assay utilized and the medium contains a quantity of the analyte that is clinically relevant, i.e., a quantity of analyte upon which medically relevant decisions may be made. In the absence of any interfering substance, this medium is called the control. A selected amount of one of IS 1-10 (IS 1, for example) is added to the medium along with the monoclonal antibody-tracer conjugate. The assay is conducted according to the protocol for the particular assay chosen. A signal is read and is related to the amount of IS 1 in the medium. The percent cross-reactivity is 100 times the apparent analyte concentration due to IS recognition ([apparent analyte]$_{IS\ present}$ minus the concentration of analyte in the control ([analyte]$_{control}$) divided by the concentration of the interfering substance [IS]. The equation therefore is:

$$\frac{100 \times ([\text{apparent analyte}]_{IS\ present} - [\text{analyte}]_{control})}{[IS]}$$

The assay is repeated for each of interfering substances IS 1-10. The assay is also repeated for each different antibody versus each different interfering substance. The results are then analyzed to choose each of the antibodies to be employed in an assay for an analyte in the sample. The apparent analyte concentration is the analyte value obtained when testing a sample containing the analyte and the IS by a test method that will detect the IS to some degree. It is not the true concentration since a test method demonstrating cross reactivity is detecting both analyte and the IS.

For example, each of antibodies A, B and C exhibit a sufficient level of binding to the analyte and are screened according to the above method. The following table is obtained.

TABLE 1

| | Percent Cross-reactivity | | |
|---|---|---|---|
| | A | B | C |
| IS 1 | 0.2 | 0.3 | 13 |
| IS 2 | 1.5 | 10 | 10 |
| IS 3 | 40 | 3 | 2 |
| IS 4 | 0.1 | 10 | 15 |
| IS 5 | 1.3 | 5 | 80 |
| IS 6 | 5 | 20 | 0.3 |
| IS 7 | 0.01 | 25 | 0.02 |
| IS 8 | 30 | 5 | 0.1 |
| IS 9 | 0.3 | 0.5 | 0.3 |
| IS 10 | 25 | 10 | 0.2 |

Monoclonal antibody A exhibits low cross-reactivity to six out of 10 interfering substances (IS 1, 2, 4, 5, 7 and 9) when compared to the cross-reactivity of monoclonal antibody B and monoclonal antibody C (with the exception of IS 9) to those same six interfering substances. Monoclonal antibody C exhibits low cross-reactivity to six of the 10 interfering substances (IS 3, 6, 7, 8, 9 and 10) when compared to the cross-reactivity of monoclonal antibody B and monoclonal antibody A (with the exception of IS 7 and IS 9) to those same six interfering substances. Moreover, monoclonal antibody A exhibits high cross-reactivity to four interfering substances (IS 3, 6, 8 and 10) when compared to the cross-reactivity of monoclonal antibody B (with the exception of IS 6) and monoclonal antibody C to those same four interfering substances whereas monoclonal antibody C exhibits high cross-reactivity to four interfering substances (IS 1, 2, 4 and 5) when compared to the cross-reactivity of monoclonal antibody B (with the exception of IS 2) and monoclonal antibody A to those same four interfering substances. As can be seen, monoclonal antibody A exhibits low cross-reactivity to the four interfering substances to which monoclonal antibody C exhibits high cross-reactivity and vice versa. Accordingly, monoclonal antibodies A and C are selected for use in an assay for the analyte in question. On the other hand, monoclonal antibody B exhibits a high level of binding reactivity to eight of the ten interfering substances when compared to the cross-reactivity of monoclonal antibody A and monoclonal antibody C to those same eight interfering substances. Accordingly, in light of the profile for monoclonal antibodies A and C, monoclonal antibody B is not selected for inclusion as a tracer conjugate reagent in an assay for the analyte where IS 1-10 are expected to be present in a sample.

The evaluation assay may be repeated using a mixture of 50% (by weight) monoclonal antibody A-tracer conjugate and 50% of monoclonal antibody C-tracer conjugate. The following table is obtained.

TABLE 2

| | Percent Cross-reactivity | | |
|---|---|---|---|
| | A | A + C | C |
| IS 1 | 0.2 | 0.3 | 13 |
| IS 2 | 1.5 | 1.7 | 10 |
| IS 3 | 40 | 3 | 2 |
| IS 4 | 0.1 | 0.2 | 15 |
| IS 5 | 1.3 | 3 | 80 |
| IS 6 | 5 | 0.4 | 0.3 |
| IS 7 | 0.01 | 0.02 | 0.02 |
| IS 8 | 30 | 0.5 | 0.1 |
| IS 9 | 0.3 | 0.3 | 0.3 |
| IS 10 | 25 | 1.1 | 0.2 |

As can be seen, the mixture of monoclonal antibody A-tracer conjugate and monoclonal antibody C-tracer conjugate exhibits a lower cross-reactivity profile to all ten of the interfering substances than either monoclonal antibody individually. Furthermore, the cross-reactivity profile demonstrates that the reduction in cross-reactivity is more than expected from the mere 50-50 combination of the two antibodies. For example, with regard to IS1, cross-reactivity of monoclonal antibody A is 0.2 and cross-reactivity of monoclonal antibody C is 13; however, the cross-reactivity of the 50-50 combination of the two antibodies is 0.3, not a number that is around the mid-point of 0.2 and 13.

The sample to be tested may be non-biological or biological. "Non-biological samples" are those that do not relate to a biological material and include, for example, soil samples, water samples, air samples, samples of other gases and mineral samples. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid.

The analyte is a substance of interest or the compound or composition to be detected and/or quantitated. The analyte may be monovalent (mono-epitopic), usually haptenic, or polyvalent (poly-epitopic) and may be a single compound or plurality of compounds that share at least one common epitopic or determinant site.

The mono-epitopic analytes or small molecule analytes have a molecular weight from about 50 to less than about 5,000, or about 50 to about 2,000, or about 100 to 2,000, or about 150 to about 2,000, or about 200 to about 2,000, or about 100 to about 1,500, or about 200 to about 1,000, for example. The analytes include hormones, steroids, drugs, metabolites, pesticides, pollutants, and the like. Representative analytes, by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., Phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine, cortisol, triiodothyronine, testosterone, estradiol, estrone, progesterone, polypeptides such as angiotensin, LHRH, and immunosuppressants such as cyclosporin, FK506, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) anti-neoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituents; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamycin, tobramycin, and amikacin; and (xviii) pesticides such as polyhalogenated biphenyls, phosphate esters, thiophosphates, carbamates, polyhalogenated sulfenamides, their metabolites and derivatives.

Poly-epitopic analytes may be, for example, poly(amino acids), i.e., polypeptides and proteins; polysaccharides; or nucleic acids; and combinations thereof. Such combinations include components of bacteria, viruses, chromosomes, genes, mitochondria, nuclei, cell membranes and the like. In some embodiments, the poly-epitopic analytes have a molecular weight of at least about 5,000, or at least about 10,000. In the poly(amino acid) category, the poly(amino acids) of interest are from about 5,000 to 5,000,000 molecular weight, or from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, for example. Such proteins include, for example, immunoglobulins, cytokines, enzymes, hormones, cancer antigens, nutritional markers, tissue specific antigens, for example. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, α-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For receptor analytes, the molecular weights will generally range from about 10,000 to about $2 \times 10^8$, or from about 10,000 to about $10^6$. For immunoglobulins, IgA, IgG, IgE and IgM, the molecular weights vary from about 160,000 to about $10^6$. Enzymes are in the range from about 10,000 to about 1,000,000 in molecular weight. Natural receptors vary widely, generally being at least about 25,000 molecular weight and may be about $10^6$ or higher molecular weight, including such materials as avidin, DNA, RNA, thyroxine binding globulin, thyroxine binding prealbumin, transcortin, for example. The term analyte further includes oligonucleotide and polynucleotide analytes such as m-RNA, r-RNA, t-RNA, DNA, and DNA-RNA duplexes, for example.

An assay medium, which in some embodiments is an aqueous buffered medium at a moderate pH, is generally one that provides optimum assay sensitivity. The aqueous medium may be solely water or may include from 0.1 to about 40 volume percent of a cosolvent such as, for example, a water miscible organic solvent, e.g., an alcohol, an ether or an amide. The pH for the medium will usually be in the range of about 4 to about 11, or in the range of about 5 to about 10, or in the range of about 6.5 to about 9.5, for example. The pH utilized is often the result of a compromise between optimum binding of the binding members of any specific binding pairs and the pH optimum for other reagents of the assay such as members of the signal producing system, for example. Various buffers may be used to achieve the desired pH and maintain the pH during the determination. Illustrative buffers include borate, phosphate, carbonate, Tris(tris(hydroxymethyl)-aminomethane), barbital, PIPES, HEPES, MES, ACES, MOPS, BICINE, and the like.

The particular buffer employed is not critical, but in an individual assay one or another buffer may be preferred.

Various ancillary materials may be employed in the assay methods. For example, in addition to buffers the medium may comprise one or more of stabilizers for the medium and for the reagents employed and salts to increase the ionic strength, for example. In some embodiments, in addition to these additives, the medium may include proteins such as, e.g., albumins; organic solvents such as, e.g., formamide; quaternary ammonium salts; polyanions such as, e.g., dextran sulfate; binding enhancers, e.g., polyalkylene glycols; polysaccharides such as, e.g., dextran, trehalose, or the like. The medium may also comprise agents for preventing the formation of blood clots. Such agents are well known in the art and include, for example, EDTA, EGTA, citrate and heparin. The medium may also comprise one or more preservatives as are known in the art such as, for example, sodium azide, neomycin sulfate, PROCLIN® 300 and Streptomycin. Any of the above materials, if employed, is present in a concentration or amount sufficient to achieve the desired effect or function.

Following the preparation of the combination of the sample and the antibodies in the medium, the medium is incubated under conditions for binding of the antibodies to the epitopic sites of the analyte and of the interfering substances as the case may be. One or more incubation periods may be applied to the medium at one or more intervals including any intervals between additions of various reagents for determining the presence and/or amount of the analyte. In many embodiments, the medium is incubated at a temperature and for a time sufficient for the above binding and for the binding and reaction of various others of the reagents to occur. Moderate temperatures are normally employed for carrying out the method. Incubation temperatures may range from about 5° to about 70° C., or from about 15° C. to about 70° C., or from about 20° C. to about 45° C., for example. The time period for the incubation is about 0.2 seconds to about 6 hours, or about 2 seconds to about 1 hour, or about 1 to about 5 minutes, for example. The time period depends on the temperature of the medium and the rate of binding of the various reagents, which is determined by the association rate constant, the concentration, the binding constant and dissociation rate constant.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents. The concentration range of interest of the analyte will generally determine the concentrations of the various reagents in the assay medium. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of the analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially.

Optionally, an incubation step may be involved subsequent to each addition as discussed above.

The medium is examined for the presence and/or amount of complexes comprising the antibodies where the presence and/or amount of the complexes indicate the presence and/or amount of the analyte in the sample, thus measuring the amount of analyte. Any convenient method may be employed to measure the amount of the complexes. The phrase "measuring the amount of analyte" refers to the quantitative, semiquantitative and qualitative determination of the analyte. Methods that are quantitative, semiquantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal are related to the presence and/or amount of the analyte in the sample. The particular mode of detection depends on one or more of the nature of the particular assay system employed and the nature of the sps member(s) employed. As discussed above, there are numerous methods by which a tracer, such as, for example, the tracer of a antibody-tracer conjugate or of other tracer reagents, can be employed to result in the generation of a signal, which in some embodiments is detectable by external means. Activation of a signal producing system depends on the nature of the signal producing system members. Luminescence or light produced as a result of activation of the signal producing system can be measured visually, photographically, actinometrically, spectrophotometrically or by any other convenient means to determine the amount thereof, which is related to the amount of analyte in the medium. The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, and the like.

Temperatures during measurements generally range from about 10° to about 70° C. or from about 20° to about 45° C., or about 20° to about 25° C. In some embodiments the temperature during measurement is substantially constant. In one approach standard curves are formed using known concentrations of the analyte. Calibrators and other controls may also be used.

General Description of Assays in which the Antibodies May be Utilized

The following discussion is by way of illustration and not limitation. The present antibodies may be employed in any assay that employs an antibody reagent. The use of antibody-tracer conjugates, by way of illustration and not limitation, has particular application to assays for low molecular weight analytes or small molecule analytes, but the conjugates also find use in assays for larger analytes. The assays can be performed either without separation (homogeneous) or with separation (heterogeneous) of any of the assay components or products. Heterogeneous assays usually involve one or more separation steps and can be competitive or non-competitive. The assays may be manual or automated.

In many embodiments immunoassays involve labeled reagents. Immunoassays that involve labeled reagents include chemiluminescence immunoassays, enzyme immunoassays, fluorescence polarization immunoassays, radioimmunoassays, inhibition assay, induced luminescence assays, and fluorescent oxygen channeling assays, for example.

One general group of immunoassays in which embodiments of the present conjugates may be employed to determine the presence and/or amount of and analyte in a sample includes immunoassays using a limited concentration of one of the assay reagents. Another group of immunoassays involves the use of an excess of one or more of the principal reagents. Another group of immunoassays are separation-free homogeneous assays in which the labeled reagents modulate the label signal upon binding of the present antibodies and an analyte in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; the induced luminescence immunoassay ("LOCI® technology") disclosed in U.S. Pat. No. 5,340,716 (Ullman, et al.); immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The above disclosures are all incorporated herein by reference.

Other enzyme immunoassays are the enzyme modulator mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), and particle enhanced turbidimetric immunoassay ("PETIA"), etc.; for example.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of a reagent upon the binding of an analyte. Such assays include, for example, optical immunosensor assays, acoustic immunosensor assays, semiconductor immunosensor assays, electrochemical transducer immunosensor assays, potentiometric immunosensor assays, and amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference.

In an embodiment of a competitive homogeneous assay, by way of example and not limitation, the antibodies are combined with a medium containing the sample suspected of containing the analyte and the analyte conjugated to an enzyme label (analyte analog) as an example of a tracer. If analyte is present, the amount of the antibodies that bind to the enzyme labeled analyte is reduced, which may result in an increase or in a reduction of the signal produced depending on the nature of the assay. The signal may be determined by conventional techniques and an increase or a reduction in the amount of signal is related to the amount of the analyte in the sample.

In another embodiment of a competitive homogeneous assay, by way of example and not limitation, antibody-tracer conjugates are combined with a medium containing the sample suspected of containing the analyte and the analyte conjugated to an enzyme label. The tracer of the antibody-tracer conjugates is a substrate for the enzyme that is reactive with the enzyme when brought into close proximity to the enzyme label by virtue of the binding of the antibody-tracer conjugates to the analyte having the enzyme label. If analyte is present, the amount of the antibody-tracer conjugates that bind to the enzyme labeled analyte is reduced, which results in a reduction of the signal produced. The signal may be determined by conventional techniques and the reduction in the amount of signal is related to the amount of the analyte in the sample.

In an embodiment of a non-competitive sandwich assay for the determination of a poly-epitopic analyte, by way or example and not limitation, antibody-tracer conjugates are employed and an immune sandwich complex is formed in an assay medium. The complex comprises the analyte or the interfering substances, the antibody-tracer conjugates and an sbp member that binds to the analyte or to the tracer of the antibody-tracer conjugates. Subsequently, the immune sandwich complex is detected by determining the presence of the tracer and the amount thereof is related to the amount of analyte in the sample.

As with the enzyme-enzyme substrate example above, many known assays utilize a signal producing system that employs first and second sps members. The sps members may be related in that activation of one member of the sps produces a product such as, e.g., light, which results in activation of another member of the sps.

In an embodiment of a heterogeneous sandwich assay by way of illustration and not limitation, an sbp member for the analyte bound to a solid support is contacted with a medium containing a sample suspected of containing the analyte. After a wash and separation step, the support is contacted with a medium containing, for example, antibody-tracer conjugates, where the tracer is, for example, an enzyme, for a second incubation period. The support is again washed and separated from the medium and either the medium or the support is examined for the presence of a signal. The presence and/or amount of signal are related to the presence and/or amount of the analyte in the sample.

In a variation of the above sandwich assay, the sample suspected of containing the analyte in a suitable medium is contacted with the antibody-tracer conjugates and incubated for a period of time. Then, the medium is contacted with an sbp member comprising a label that is reactive with the tracer of the antibody-tracer conjugates or where a product of the activation of the label or the tracer is reactive with the tracer or the label as the case may be. After an incubation period, the support is separated from the medium and washed to remove unbound reagents. The support or the medium is examined for the presence of a signal, which is related to the presence or amount of analyte. In another variation of the above, the sample, the antibody-tracer conjugates and the labeled sbp member are combined in a medium and incubated in a single incubation step. Separation, wash steps and examination for signal are as described above. In one embodiment of the variation discussed above, the signal is determined without a separation step.

In some embodiments of known assays, the sps members comprise a sensitizer such as, for example, a photosensitizer, and a chemiluminescent composition where activation of the sensitizer results in a product that activates the chemiluminescent composition. One sps member usually generates a detectable signal that relates to the amount of bound and/or unbound sps member, i.e. the amount of sps member bound or not bound to the analyte being detected or to an agent that reflects the amount of the analyte to be detected. In accordance with embodiments of the present invention, the tracer employed, for example, in antibody-tracer conjugates, may be one of either the sensitizer reagent or the chemiluminescent reagent or may be an sbp member that binds to a complementary sbp member that comprises either the sensitizer or the chemiluminescent reagent. An embodiment of such an assay is the induced luminescence immunoassay (LOCI). As indicated above, the induced luminescence immunoassay is described in U.S. Pat. No. 5,340,716 (Ullman), which disclosure is incorporated herein by reference.

A chemiluminescent compound (chemiluminescer) is a compound that is chemically activatable and, as a result of such activation, emits light at a certain wavelength. Examples of chemiluminescers, by way of illustration and not limitation, include olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as luminol; and aromatic compounds that can form endoperoxides, for example. As a consequence of the activation reaction, the chemiluminescers directly or indirectly cause the emission of light.

A sensitizer is a molecule, usually a compound, for generation of a reactive intermediate such as, for example, singlet oxygen, for activation of a chemiluminescent compound. In some embodiments, the sensitizer is a photosensitizer. Other sensitizers that can be chemi-activated (by, e.g., enzymes and metal salts) include, by way of example and not limitation, other substances and compositions that can produce singlet oxygen with or, less preferably, without activation by an external light source. For example, certain compounds have been shown to catalyze the conversion of hydrogen peroxide to singlet oxygen and water. Also included within the scope of photosensitizers are compounds that are not true sensitizers but which on excitation by heat, light, ionizing radiation, or chemical activation will release a molecule of singlet oxygen. Members of this class of compounds include, for example, the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A photosensitizer is a sensitizer for activation of a photoactive compound, for example, by generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of 200 to 1,100 nm, or 300 to 1,000 nm, or 450 to 950 nm, with an extinction coefficient at its absorbance maximum greater than 500 $M^{-1}$ $cm^{-1}$, or greater than 5,000 $M^{-1}$ $cm^{-1}$, or greater than 50,000 $M^{-1}$ $cm^{-1}$, at the excitation wavelength. Photosensitizers should be relatively photostable and, preferably, not react efficiently with singlet oxygen. Examples of photosensitizers, by way of illustration and not limitation, include acetone, benzophenone, 9-thioxanthone, eosin, 9,10-dibromoanthracene, methylene blue, metallo-porphyrins, such as hematoporphyrin, phthalocyanines, chlorophylls, rose bengal, and buckminsterfullerene, for example, and derivatives of these compounds.

Examples of chemiluminescent compounds and photosensitizers that may be utilized in embodiments of assays employing the present tracer conjugates are set forth in U.S. Pat. No. 5,340,716 (Ullman, et al.), the relevant portions of which disclosure are incorporated herein by reference.

Some assays in which the present antibodies may be employed utilize a support with which one or more reagents such as the tracer or an antibody or an antibody-tracer conjugate may be associated. The support may be solid or semi-solid and may be comprised of an organic or inorganic, water insoluble material, which may be transparent or partially transparent. The solid support has a surface that is hydrophobic and can have any of a number of shapes such as, for example, particulate, including beads and particles, film, membrane, tube, well, strip, rod, and planar surfaces such as, e.g., plate. Depending on the type of assay, the solid support may or may not be suspendable in the medium in which it is employed. Examples of a suspendable solid support include polymeric materials such as latex particles and magnetic particles. Other solid support compositions include polymers, such as poly(vinyl chloride), polyacrylamide, polyacrylate, polyethylene, polypropylene, poly-(4-methylbutene), polystyrene, polymethacrylate, poly(ethylene terephthalate), nylon, and poly(vinyl butyrate), for example; either used by themselves or in conjunction with other materials.

In some embodiments the support is a particle. The particles generally have an average diameter of about 0.02 to about 100 microns, or about 0.05 to about 100 microns, or about 0.1 to about 100 microns, or about 0.5 to about 100 microns, or about 0.02 to about 50 microns, or about 0.05 to about 50 microns, or about 0.1 to about 50 microns, or about 0.5 to about 50 microns, or about 0.02 to about 20 microns, or about 0.05 to about 20 microns, or about 0.1 to about 20 microns, or about 0.5 to about 20 microns, for example. In some embodiments, the particles have an average diameter from about 0.05 microns to about 20 microns or from about 0.3 microns to about 10 microns, or about 0.3 microns to about 5 microns, for example. In some embodiments, the particles are latex particles or chrome particles.

A latex particle is a particulate water suspendable, water insoluble polymeric material. In some embodiments the latex is a substituted polyethylene such as polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like.

Polymeric particles can be formed from addition or condensation polymers. The particles will be readily dispersible in an aqueous medium and can be functionalizable so as to permit conjugation to one or more of an sps member and an sbp member, for example. The particles can also be derived from naturally occurring materials, naturally occurring materials that are synthetically modified, and synthetic materials. In some embodiments the particles have, either naturally occurring or synthetically introduced, a reactive functionality such as, for example, amine groups, which are reactive with a corresponding reactive functionality such as, for example, aldehyde groups.

As mentioned above, the tracer or another assay reagent may be associated with the support. The manner of association of the tracer or the reagent with a support depends on one or more of the nature of the support, the nature of the reagent, the surface area and porosity of the support and the nature of any solvent employed, for example. The association may be by adsorption of the reagent by the support, covalent bonding of the reagent to the support, dissolution or dispersion of the reagent in the solid support, non-covalent bonding of the reagent to the support by means of binding pair members (e.g., avidin-biotin and digoxin-antibody for digoxin), for example. In this manner the reagent is "associated with" the solid support.

Association of a reagent such as, for example, a sensitizer or a chemiluminescent compound, with latex particles may involve incorporation during formation of the particles by polymerization, or incorporation into preformed particles, e.g., by non-covalent dissolution into the particles, for example. In some approaches a solution of the reagent is employed. Solvents that may be utilized include, for example, alcohols, including, e.g., ethanol, ethoxyethanol, methoxyethanol, ethylene glycol and benzyl alcohol; amides such as, e.g., dimethyl formamide, formamide, acetamide and tetramethyl urea; sulfoxides such as, e.g., dimethyl sulfoxide and sulfolane; and ethers such as, e.g., carbitol, ethyl carbitol and dimethoxy ethane; and water; and mixtures of two or more of the above. The use of solvents having high boiling points in which the particles are insoluble permits the use of elevated temperatures to facilitate dissolution of the compounds into the particles and are particularly suitable. The solvents may be used singly or in combination. A solvent should be selected that does not interfere with the signal producing ability of the reagent because of its intrinsic properties or ability to be removed from the particles. In some embodiments aromatic solvents may be employed such as, for example, dibutylphthalate, benzonitrile, naphthonitrile, dioctylterephthalate, dichlorobenzene, diphenylether and dimethoxybenzene.

Generally, the temperature employed during the procedure is chosen to maximize the amount of signal from the sps member particles with the proviso that the particles should not melt or become aggregated at the selected temperature. In some embodiments, elevated temperatures are employed. The temperatures for the procedure may range from about 20° C. to about 200° C., or from about 50° C. to about 170° C., for example. It has been observed that some compounds that are nearly insoluble at room temperature are soluble in, for example, low molecular weight alcohols, such as ethanol and ethylene glycol, for example, at elevated temperatures. Carboxylated modified latex particles have been shown to tolerate low molecular weight alcohols at such temperatures.

In one example of a competitive induced luminescence immunoassay by way of example and not limitation, the assay uses a particle associated with a photosensitizer and a first sbp member, for example, a binding partner for biotin such as, e.g., avidin or streptavidin. The chemiluminescent reagent comprises an analyte analog. A third reagent comprises antibody-tracer conjugates where the tracer is a second sbp member that is complementary to the first sbp member such as, for example, biotin. The chemiluminescent reagent comprising the analyte analog competes with the analyte in a sample for binding to the antibody-tracer conjugates. Thus, the more analyte in the sample, the greater is the reduction in the signal produced by the photosensitizer and the chemiluminescent compound coming into close proximity by virtue of binding of the antibody-tracer conjugates to the chemiluminescent reagent comprising the analyte analog. The photosensitizer generates singlet oxygen and activates the chemiluminescent reagent when the two labels are in close proximity. The activated chemiluminescent reagent subsequently produces light. The amount of light produced is inversely related to the amount of the complex formed between the analyte and the photosensitizer reagent and the chemiluminescent reagent, which in turn is related to the amount of analyte present.

In another example of an induced luminescence immunoassay by way of example and not limitation, the assay uses a particle associated with a photosensitizer and a first sbp member, for example, a binding partner for the analyte. The chemiluminescent reagent comprises a second sbp member. In accordance with present embodiments, either the photosensitizer reagent or the chemiluminescent reagent may be, for example, antibody-tracer conjugates where the tracer is either the photosensitizer or the chemiluminescent compound. The sbp members bind to the analyte to form a complex, or the first sbp member binds to the second sbp member to form a complex, in relation to the presence of the analyte in the medium. If the analyte is present, the photosensitizer and the chemiluminescent compound come into close proximity by virtue of the binding based on the presence of the analyte. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of analyte present.

In some embodiments of the induced luminescence assay by way of illustration and not limitation, a photosensitizer particle is employed that is conjugated to avidin or streptavidin. A biotinylated sbp member that binds to the analyte is also employed. In this exemplary embodiment a chemiluminescent reagent is also employed, which comprises an sbp member that binds to the analyte. In accordance with present embodiments either the biotinylated sbp member or the chemiluminescent reagent may be represented by the antibody-tracer conjugates. The reaction medium is incubated to allow the photosensitizer particles to bind to the biotinylated sbp member by virtue of the binding between avidin and biotin and to also allow the binding partner for the analyte to bind to the analyte. Then, the medium is irradiated with light to excite the photosensitizer, which is capable in its excited state of activating oxygen to a singlet state. Because the chemiluminescent reagent is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence and/or amount of the analyte.

In some embodiments of the induced luminescence assay for a poly-epitopic analyte by way of illustration and not limitation, a photosensitizer particle is employed that is conjugated to avidin or streptavidin. A biotinylated sbp member that binds to the analyte is also employed. In this exemplary embodiment a chemiluminescent reagent is also employed, which comprises an analyte analog. In accordance with present embodiments either the biotinylated sbp member or the chemiluminescent reagent may be represented by, for example, antibody-tracer conjugates. The reaction medium is incubated to allow the photosensitizer particles to bind to the biotinylated sbp member by virtue of the binding between avidin and biotin and to also allow the binding partner for the analyte to bind to the analyte or to the analyte analog. Then, the medium is irradiated with light to excite the photosensitizer, which is capable in its excited state of activating oxygen to a singlet state. The presence of the analyte results in less chemiluminescent reagent in close proximity to the photosensitizer and, thus, the amount of reduction in signal (luminescence) resulting from the activation of the chemiluminescent reagent by the singlet oxygen. The medium is then examined for the presence and/or the amount of luminescence or light emitted, the reduction in the amount thereof being related to the presence and/or amount of the poly-epitopic analyte.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

Kits Comprising Reagents for Conducting Assays

Embodiments of the present antibodies and antibody-tracer conjugates and other reagents for conducting a particular assay for an analyte may be present in a kit useful for conveniently performing an assay for the determination of an analyte. In some embodiments a kit comprises in packaged combination two or more antibodies or antibody-tracer conjugates. The kit may also include members of a signal producing system other than the tracer. In some embodiments the tracer is a small molecule such as, for example, biotin, and the members of the signal producing system include a binding partner for the small molecule, such as, for example, avidin, streptavidin or an antibody specific for biotin where the binding partner is bound to a label. For example, when the signal producing system involves a photosensitizer and a chemiluminescent compound, the binding partner for biotin may be linked to the photosensitizer or to the chemiluminescent compound. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, sps members and ancillary reagents, for example.

The relative amounts of the various reagents in the kits can be varied widely to provide for concentrations of the reagents that substantially optimize the reactions that need to occur during the assay methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay utilizing embodiments of the present conjugates. The kit can further include a written description of a method as described above.

Definitions

The following definitions as used in this specification and the appended claims are provided for terms and phrases not otherwise specifically defined above. It is to be understood that the terminology used herein is for the purpose of describing particular embodiments only and is not intended to be limiting.

The phrase "at least" as used herein means that the number of specified items may be equal to or greater than the number recited.

The phrase "about" as used herein means that the designated value may vary by plus or minus twelve percent, or eleven percent, or ten percent, or nine percent, or eight percent, or seven percent, or six percent, or five percent, or four percent, or three percent, or two percent, or one percent. For example, "about 5" with a variance of plus or minus 10% means a range of 4.5 to 5.5.

The designations "first" and "second" are used solely for the purpose of differentiating between two items such as, for example, "first sps member" and "second sps member," or "first sbp member" and "second sbp member" and are not meant to imply any sequence or order or importance to one item over another or any order of addition, for example.

The singular forms "a", "an" and "the" include plural referents unless the content clearly dictates otherwise.

The term "substantially" when not specifically defined above varies with the context as understood by those skilled in the relevant art and generally means at least 70%, or at least 80%, or least 90%, or at least 95%, or at least 99%, or 100%.

"Optionally" means that the specified item may be present or may not be present.

"Analyte analog" is a modified analyte, which can compete with the analogous analyte for a receptor, the modification providing means to join an analyte analog to another molecule. The analyte analog will usually differ from the analyte by more than replacement of a hydrogen with a bond that links the analyte analog to another molecule, but need not. The analyte analog can bind to a receptor or binding partner for the analyte in a manner similar to the analyte. The analog may be, for example, a label conjugate of the analyte, a particle conjugate of the analyte, and an antibody directed against the idiotype of an antibody to the analyte, for example.

The following examples further describe specific embodiments of the invention by way of illustration and not limitation and are intended to describe and not to limit the scope of the invention. Parts and percentages disclosed herein are by volume unless otherwise indicated.

As used herein, the phrase "associated with" includes covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

EXAMPLES

Materials

Unless indicated otherwise, reagents were purchased from Sigma-Aldrich (Milwaukee, Wis.) and used as received.

ABBREVIATIONS

LOCI® assay—luminescent oxygen channeling immunoassay

HEPES—hydroxyethyl piperazine-ethanesulfonic acid

HEPES diluent, pH 7.2-57.5 mM in water with 20.15 mg/mL NaCl, 0.428 mg/mL EDTA, 1.15 mg/mL Triton X-405, 1.73 mg/mL PROCLIN® 300 preservative and 0.12 mg/mL Neomycin, adjusted to pH 7.2

HEPES diluent pH 8.0-57.5 mM in water with 20.15 mg/mL NaCl, 0.428 mg/mL EDTA, 1.15 mg/mL TRITON® X-405, 1.73 mg/mL PROCLIN® 300 and 0.12 mg/mL Neomycin, adjusted to pH 8.0

Antibody Dialysis Buffer—10 mM $NaH_2PO_4$, $Na_2HPO_4$, pH 7.0, 300 mM NaCl

ProSep Protein A Binding Buffer—obtained from Fisher Scientific (Pittsburgh, Pa.)

CMO—carboxymethoxyoxime

EDAC—1-ethyl-3-(3-dimethylaminopropyl)carbodiimide hydrochloride

EDTA—ethylenediaminetetraacetate

NHS—N-hydroxysuccinimide

TLC—thin layer chromatography

HPLC—high performance liquid chromatography

MeOP—1-methoxy-2-propanol

UPA instrument—particle size analyzer, UPA Instruments, West Chester, Ohio Steroid-stripped serum—purchased from Bioreclamation LLC (Westbury N.Y.) and spiked with cortisol to achieve a sample at the medical decision level, which was free from cross-reactants MES—2-(N-morpholino)ethanesulfonic acid MES buffer—50 mM MES pH 6 Buffer, 5% MeOP and 0.1% TWEEN 20®

Hapten Wash Buffer—57.5 mM HEPES, Na HEPES, 17.5 mg/mL NaCl, 0.372 mg/mL EDTA, 0.12 mg/mL neomycin sulfate, 1 mg/mL Triton X 405, 1.73 mg/mL PROCLIN® 300 hrs—hours min—minutes w/w—weight to weight mL—milliliters mg—milligrams g—grams mM—millimolar EPRM chemibead—EPRM chemibead (chemibead) was prepared in a manner similar to the method described in U.S. Pat. No. 6,153,442 and U.S. Patent Application Publication No. 20050118727A, the relevant disclosures of which are incorporated herein by reference. The EPRM chemibead comprises an aminodextran inner layer and a dexal outer layer having free aldehyde functionalities. Dexal is dextran aldehyde; see, for example, U.S. Pat. Nos. 5,929,049 and 7,172,906. The reaction is carried out at a temperature of about 0 to about 40° C. for a period of about 16 to about 64 hours at a pH of about 5.5 to about 7.0, or about 6, in a buffered aqueous medium employing a suitable buffer such as, for example, MES or the like. The reaction is quenched by addition of a suitable quenching agent such as, for example, carboxymethoxyoxime (CMO), or the like and subsequent washing of the particles. The chemiluminescent compound was 2-(4-(N,N, di-tetradecyl)-anilino-3-phenyl thioxene.

APRM chemibead—a polystyrene bead with chelated europium and thioxene as the chemiluminescent composition. The APRM chemibead is prepared in a manner similar to the method described in U.S. Pat. No. 6,153,442, the relevant disclosure of which is incorporated herein by reference. The APRM chemibead comprises an aminodextran layer having free amine functionalities. The reaction is carried out at a temperature of about 0 to about 40° C., for a period of about 8 to about 24 hours.

Chemibead Reagent—hydrocortisone-3-CMO (hapten) conjugated to APRM beads in a ratio of 0.12:50 hapten: APRM. The concentrated Chemibead Reagent was diluted to a final concentration of 50 μg/mL in HEPES diluent, pH 7.2.

Sensibead Reagent—latex particle comprising a photosensitizer dye (bis-(trihexyl)-silicon-t-butyl-phthalocyanine) prepared using a method analogous to that described in U.S. Pat. Nos. 6,153,442, 7,022,529, 7,229,842 and U.S. Patent Application Publication No. 20050118727A, the relevant disclosures of which are incorporated herein by reference. The Sensibeads were diluted in HEPES diluent, pH 7.2, to a final concentration of 700 µg/mL.

Preparation of Reagents

Antibody A specific for cortisol was prepared from clone 16DC/17.7, isotype IgG1κ, accordingly to standard somatic cell hybridization procedures discussed above. Antibody L specific for cortisol consisted of clone XM210, purified monoclonal, isotype IgG2a, from HyTest Ltd (Turku, Finland). The antibodies were subjected to analytical size exclusion chromatography prior to any manipulations.

The antibodies were biotinylated using a 30:1 molar ratio of NHS-PEO$_4$-biotin (Pierce Chemical Company, Rockford Ill., part number 21330) to intact IgG1 (alternately the F(ab')$_2$ moiety can be used). NHS-PEO$_4$-Biotin was dissolved fresh at 10 mg/mL in Antibody Dialysis Buffer. A total of 700 µL of this 10 mg/mL solution was added to 13.5 mL volume of 2.93 mg/mL IgG1 (or F(ab')$_2$) solution, resulting in a 30:1 biotin:F(ab')$_2$ molar ratio. The mixture was rocked at 25° C. for exactly 3 hours. A 200 mM solution of glycine was prepared by dissolving 750 mg glycine in Antibody Dialysis Buffer to a total volume of 50 mL. At the end of the 3-hour biotinylation reaction, 1.52 mL of the 200 mM glycine solution was added to the reaction mixture. The quenched reaction mixture was rocked an additional 60 minutes at 25° C.

The biotinylated antibody was then purified using preparatory HPLC using Antibody Dialysis Buffer as the mobile phase. Fractions containing the biotinylated antibody were pooled, excluding fractions containing the trace of high molecular weight aggregates. This reagent was designated as the Biotinylated Antibody Reagent.

F(ab')$_2$ fragments were prepared by means of enzymatic digestion according to well known procedures.

EPRM chemibeads conjugated to cortisol were prepared as follows: 1 mg hydrocortisone-3-CMO was added to a 2 mL vial (first vial) equipped with a stir bar. To a second vial was added EDAC (15 mg) and NHS (15 mg) plus 1.2 mL dry acetonitrile; 200 µL of this EDAC/NHS solution was added to the first vial. The mixture was allowed to stir at room temperature until TLC indicated complete conversion to EPRM-EDA. To a 5 mL centrifuge tube was added 4.16 mL (110 mg) EPRM-EDA followed by 53 µL (0.26 mg) activated hydrocortisone-3-CMO. The centrifuge tube was allowed to rock overnight at room temperature. The mixture was transferred to a 40 mL centrifuge tube. MES buffer, pH 6, containing 5% MeOP and 0.1% TWEEN® 20 was added to bring volume in tube to 35 mL. The tube was centrifuged at 19000 rpm for 30 minutes. Supernatant was decanted. Beads were re-suspended in 1 mL buffer mixture with a stir-rod. More buffer mixture was added to bring tube volume to 35 mL. The tube in ice was sonicated at 18-21 Watts power for 30 seconds. The beads were centrifuged as above with a total of four MES-MeOP-TWEEN® 20 buffer washes being performed. After the last wash, the beads were resuspended in 1 mL Hapten Wash Buffer instead of the MES buffer mixture as above. Two more washes were performed. The beads were resuspended in sufficient Hapten Wash Buffer to give a 5 mg/mL suspension. Beads were sonicated at 50% power (cup sonicator) for 30 seconds. Particle size was tested on a UPA instrument at a wavelength of 270 nm.

Screening Assay

The assay used for screening purposes was conducted on the DIMENSION® VISTA® instrument (system) (Siemens Healthcare Diagnostics Inc., Newark Del.). Initially, 20 µL Biotinylated Antibody Reagent with 15 µL system water was added to the vessel. After 22 seconds, 15 µL sample with 15 µL system water were added to the vessel. After almost 4 minutes, 20 µL Chemibead Reagent with 15 µL system water were added to the vessel. Approximately 7 minutes later, 20 µL Sensibead Reagent with 135 µL system water was added to the vessel. The LOCI® read was taken after approximately 5 minutes. The assay from the first reagent addition to the final read took approximately 16 minutes. The contents of the vessel when the final read is taken were as follows: 2 ng/mL Biotinylated Antibody Reagent, 4 µg/mL Chemibead Reagent, 56 µg/mL Sensibead Reagent, and 40 mL/mL sample. The assay is a competitive format, which means that the greater the concentration of analyte in the sample, the smaller is the signal generation. This is because a detectable complex is formed by the Biotinylated Antibody Reagent, Chemibead Reagent, and Sensibead Reagent in the absence of analyte. The presence of analyte decreases the proportion of Biotinylated Antibody Reagent that is free to form detectable complexes.

Initial testing used Biotinylated Antibody A Reagent with the other reagents and the methodology described above to analyze the steroid-stripped serum with cortisol. The panel of 34 cross-reactants were individually added to the steroid-stripped serum with a defined concentration of cortisol (5 ng/dL) and assayed. Cross-reactivity data were calculated as follows:

$$\frac{100 \times ([\text{apparent cortisol}] \text{ in ng/dL}_{cross-reactant} - [\text{cortisol}] \text{ in ng/dL}_{control})}{\text{concentration of cross-reactant in ng/dL}}$$

The same testing was performed using Biotinylated Antibody L Reagent. The compilation of the percent cross-reactivities for the 34 compounds is referred to as the cross-reactivity profile. The apparent cortisol concentration is the cortisol value obtained when testing a sample containing cortisol and the interfering substance by the above test method that also detects the interfering substance to some degree. It is not the true concentration since a test method demonstrating cross reactivity is detecting both cortisol and the interfering substance. In this example, the apparent concentration (cortisol and interfering substance) is higher than the concentration of cortisol alone.

Figure 2:
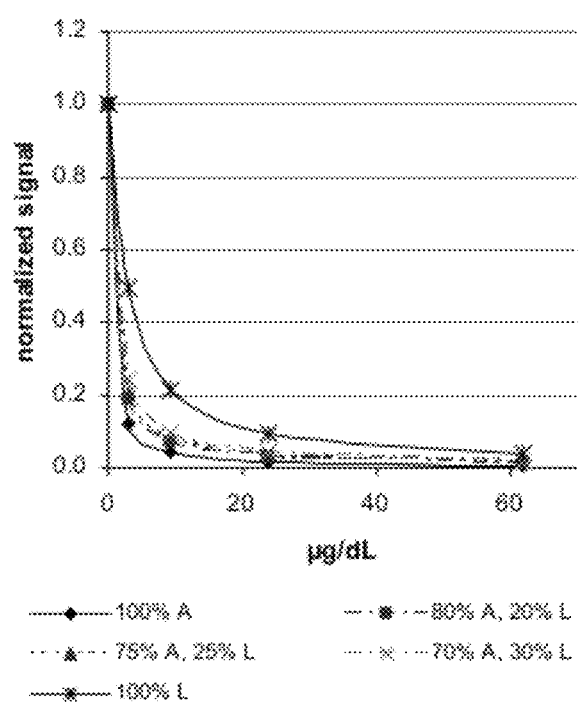
FIG. 2 is a normalized calibration curve of FIG. 1.

A further study was performed by mixing Biotinylated Antibody A Reagent with Biotinylated Antibody L Reagent in a 50:50 mixture; 80% Biotinylated Antibody A Reagent: 20% Biotinylated Antibody L Reagent; 75% Biotinylated Antibody A Reagent: 25% Biotinylated Antibody L Reagent; and 70% Biotinylated Antibody A Reagent: 30% Biotinylated Antibody L Reagent. The calibration curves and normalized calibration curves are shown in FIGS. 1 and 2, respectively. The curves demonstrate that signal can be modulated using a method in accordance with the present embodiments. The combination of two biotinylated antibodies did not have any adverse effect on the calibration curve. The curves of the intermediate ratios tested fell in between the curves of the single antibodies employed. These reagents were used to test cross-reactivity in stripped serum with cortisol. The cross-reactivity profiles are shown in Table 3

(percent cross reactivity is reported for five assay configurations using varying ratios of antibodies A and L). Each of the intermediate ratios yields a cross-reactivity profile that is better than either individual antibody. Furthermore, the cross-reactivity profile demonstrates that the reduction in cross-reactivity is more than expected from the combination of the two antibodies. For example, with regard to cortisone, percent cross-reactivity using 100% Biotinylated Antibody Reagent A is 41.7 and percent cross-reactivity using 100% Biotinylated Antibody Reagent L is 1.4; however, the percent cross-reactivity of the 75-25 combination of the two biotinylated antibody reagents is 2.8. The incorporation of 25% Biotinylated Antibody Reagent L is enough to decrease the percent cross-reactivity to cortisone by greater than 90%. Additionally, the antibody ratio proved to be quite robust, as varying the antibody percent composition by relatively small amounts had a minimal effect on the percent cross-reactivity profile.

TABLE 3

| | Biotinylated Antibody | 100% A | 80% A 20% L | 75% A 25% L | 70% A 30% L | 100% L |
|---|---|---|---|---|---|---|
| Interfering Substance | Aldosterone | 0.3 | 0.3 | 0.3 | 0.3 | 0.3 |
| | allotetrahydrocortisol | 4.7 | 6.0 | 6.5 | 7.1 | 8.1 |
| | corticosterone | 0.6 | 1.4 | 1.5 | 1.8 | 3.0 |
| | cortisone | 41.7 | 3.1 | 2.8 | 2.5 | 1.4 |
| | α-cortol | 0.2 | 0.5 | 0.6 | 0.7 | 1.0 |
| | β-cortol | 0.0 | 0.0 | 0.0 | 0.0 | 0.0 |
| | α-cortolone | 0.0 | 0.0 | 0.0 | 0.0 | 0.0 |
| | β-cortolone | 0.0 | 0.0 | 0.0 | 0.0 | 0.0 |
| | dehydrocorticosterone | 0.6 | 0.7 | 0.7 | 0.7 | 0.8 |
| | 11-deoxycorticosterone | 0.7 | 0.8 | 0.8 | 0.8 | 0.8 |
| | 11-deoxycortisol | 39.8 | 3.7 | 3.2 | 3.0 | 1.7 |
| | 21-deoxycortisol | 8.3 | 6.9 | 6.9 | 7.2 | 6.4 |
| | 21-deoxycortisone | 36.4 | 3.1 | 2.7 | 2.5 | 1.4 |
| | dexamethasone | 0.1 | 0.8 | 1.0 | 1.3 | 14.8 |
| | 5β-dihydrocortisol | 0.4 | 0.8 | 0.9 | 1.0 | 1.3 |
| | 20α-dihydrocortisol | 0.4 | 0.6 | 0.6 | 0.7 | 0.9 |
| | 20β-dihydrocortisol | 0.6 | 1.3 | 1.5 | 1.6 | 2.1 |
| | 20α-dihydrocortisone | 1.5 | 0.5 | 0.5 | 0.4 | 0.2 |
| | 20β-dihydrocortisone | 0.1 | 0.1 | 0.1 | 0.1 | 0.1 |
| | fluorocortisone acetate | 35.3 | 17.0 | 20.9 | 27.8 | 69.3 |
| | 6β-hydroxycortisol | 2.7 | 5.5 | 6.2 | 6.9 | 100.0 |
| | 11β-hydroxy-etiocholanolone | 0.0 | 0.0 | 0.0 | 0.0 | 0.0 |
| | 17β-hydroxypregnenolone | 0.1 | 0.1 | 0.1 | 0.1 | 0.1 |
| | 17α-hydroxyprogesterone | 24.1 | 2.1 | 1.8 | 1.6 | 0.9 |
| | 11β-hydroxyprogesterone | 0.6 | 0.6 | 0.7 | 0.7 | 0.7 |
| | 11-ketoetiocholanolone | 0.0 | 0.0 | 0.0 | 0.0 | 0.0 |
| | 6-methyl-prednisolone | 6.4 | 7.2 | 7.5 | 8.3 | 10.7 |
| | prednisolone | 13.6 | 12.4 | 12.2 | 12.4 | 10.2 |
| | prednisone | 26.5 | 1.5 | 1.3 | 1.1 | 0.6 |
| | progesterone | 0.6 | 0.6 | 0.6 | 0.6 | 0.6 |
| | sulphate 21-cortisol | 22.5 | 0.9 | 0.7 | 0.6 | 0.2 |
| | tetrahydrocortisol | 0.0 | 0.0 | 0.1 | 0.1 | 0.1 |
| | tetrahydrocortisone | 0.5 | 0.3 | 0.2 | 0.2 | 0.1 |
| | tetrahydro-11-deoxycortisol | 0.3 | 0.2 | 0.2 | 0.2 | 0.2 |

Based on the above experiments a calibration curve was constructed and is shown in FIGS. 1 and 2. The two biotinylated antibodies employed in the LOCI® assay system described above minimized cross reactivity and optimized the standard curve (using a logit fit function). FIG. 1 is a calibration curve showing instrument signal plotted as a function of the concentration of cortisol. FIG. 2 is a normalized calibration curve of FIG. 1. As can be seen, the curves of the intermediate ratios tested fell between the curves of the single antibodies employed and demonstrate an optimized cross reactivity profile.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for determining an amount of cortisol in a sample suspected of containing cortisol and different interfering substances, the method consisting essentially of:
   (a) combining in an aqueous medium:
      (i) the sample, and
      (ii) two or more different antibody-tracer conjugates wherein the tracer of each different conjugate is the same and wherein the antibody of each different conjugate is different and wherein each different antibody binds to at least two different epitopic sites wherein one of the epitopic sites is a binding site of cortisol that is a common binding site bound by all of the antibodies, and another of the epitopic sites is a binding site of one or more of the interfering substances that is a non-common binding site that is different for each different antibody and wherein each different antibody of the antibody-tracer conjugates is preselected for its binding profile to cortisol and to one or more of the interfering substances and wherein each different antibody exhibits a binding affinity to a portion of the interfering substances wherein the portion of interfering substances comprises about 10% to about 90% of the total number of interfering substances in a sample and wherein the number of interfering substances in one portion that have low binding affinity for two different antibodies is no greater than about 10 and wherein low binding affinity means that an interfering substance has a binding affinity for one of the antibodies that is no greater than about 80% of the binding affinity of cortisol for said one of the antibodies,
- (b) incubating the medium under conditions for binding of the different antibodies to the epitopic sites,
- (c) examining the medium for an amount of signal from the complexes comprising the epitopic sites and the antibody-tracer conjugates, and
- (d) comparing the amount of the signal to a calibration curve to determine the true amount of cortisol in the sample, wherein the interfering substances are selected from the group consisting of aldosterone, allotetrahydrocortisol, corticosterone, cortisone, α-cortol, β-cortol, α-cortolone, β-cortolone, dehydrocorticosterone, 11-deoxycorticosterone, 11-deoxycortisol, 21-deoxycortisol, 21-deoxycortisone, dexamethasone, 5β-dihydrocortisol, 20α-dihydrocortisol, 20β-dihydrocortisol, 20α-dihydrocortisone, 20β-dihydrocortisone, fluorocortisone acetate, 6β-hydroxycortisol, 11β-hydroxy-etiocholanolone, 17β-hydroxypregnenolone, 17α-hydroxyprogesterone, 11β-hydroxyprogesterone, 11-ketoetiocholanolone, 6-methyl-prednisolone, prednisolone, prednisone, progesterone, sulphate 21-cortisol, tetrahydrocortisol, tetrahydrocortisone, and tetrahydro-11-deoxycortisol.

2. The method according to claim 1 wherein the sample is a body excretion, body aspirant, body excisant or body extractant.

3. The method according to claim 1 wherein the tracer is a member of a signal producing system, a member of a specific binding pair, or a complex of members of a specific binding pair.

4. The method according to claim 1 wherein the method is a homogeneous assay method.

5. The method according to claim 1 wherein the antibodies are preselected by a process comprising conducting for each antibody an assay for cortisol in an assay medium comprising cortisol and one of the interfering substances and determining a percent cross-reactivity of the antibody for the interfering substance and repeating the assay for each different interfering substance to prepare a cross-reactivity profile and selecting for use in the method the two or more different antibodies.

* * * * *